United States Patent
Pasquier et al.

(10) Patent No.: US 7,553,337 B2
(45) Date of Patent: *Jun. 30, 2009

(54) HAIR COLORANTS FOR SIMULTANEOUS DYEING AND BRIGHTENING OF KERATIN FIBERS

(75) Inventors: Cecile Pasquier, Marly (CH); Caroline Kiener, Marly (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 412 days.

This patent is subject to a terminal disclaimer.

(21) Appl. No.: 10/587,763

(22) PCT Filed: Nov. 16, 2005

(86) PCT No.: PCT/EP2004/012982

§ 371 (c)(1),
(2), (4) Date: Jul. 28, 2006

(87) PCT Pub. No.: WO2005/079732

PCT Pub. Date: Sep. 1, 2005

(65) Prior Publication Data

US 2007/0169284 A1     Jul. 26, 2007

(30) Foreign Application Priority Data

Feb. 21, 2004   (DE)   ................ 10 2004 008 604

(51) Int. Cl.
*A61Q 5/10* (2006.01)
*C09B 44/08* (2006.01)

(52) U.S. Cl. .................. 8/405; 8/406; 8/437; 8/455; 8/466; 8/570; 8/571; 8/575; 534/604

(58) Field of Classification Search .................. 8/405, 8/406, 437, 455, 466, 570, 571, 575; 534/604
See application file for complete search history.

(56) References Cited

U.S. PATENT DOCUMENTS 4,046,752 A * 9/1977 Hohmann et al. ........... 534/607
4,269,768 A   5/1981 Neeb et al.

FOREIGN PATENT DOCUMENTS

| DE | 28 22 912 | 11/1979 |
|---|---|---|
| DE | 36 02 587 | 7/1987 |
| DE | 101 18 271 | 3/2002 |

* cited by examiner

*Primary Examiner*—Eisa B Elhilo
(74) *Attorney, Agent, or Firm*—Michael J. Striker

(57) ABSTRACT

The present invention has for an object agents for the simultaneous brightening and coloring of keratin fibers—particularly hair—which are characterized in that (a) they contain an oxidant and (b) at least one thiazolium dye of formula (I) and that (c) they have a basic pH (I)

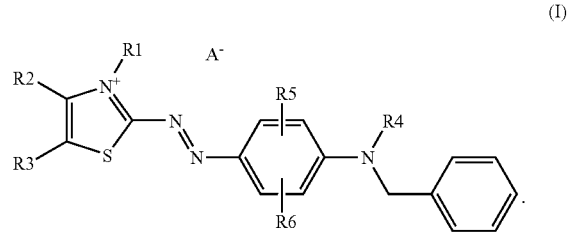

12 Claims, No Drawings

HAIR COLORANTS FOR SIMULTANEOUS DYEING AND BRIGHTENING OF KERATIN FIBERS

CROSS-REFERENCE TO RELATED APPLICATIONS

This application is the national stage entry of PCT/EP04/12982, filed 16 Nov. 2005 and claims priority under 35 U.S.C. 119(a)-(d) to German Patent Application DE 10 2004 008 604.4, filed 21 Feb. 2004.

BACKGROUND OF THE INVENTION

1. Field of the Invention

The present invention has for an object agents for the simultaneous dyeing and brightening of keratin fibers, for example wool, silk or hair and particularly human hair, and which contain at least one thiazolium dye.

2. Description of Related Art

Two coloring methods are usually used for the color-changing treatment of keratin fibers. By the first method, the coloring is accomplished with oxidative or permanent colorants and by the use of a mixture of different developers and couplers and an oxidant. By this method, if necessary, a direct (non-oxidative) dye can be added if the coloring result is to be adjusted or special coloring effects are to be achieved. The second method involves the exclusive use of direct dyes which in an appropriate carrier composition are applied to the fibers. This method is easy to apply, very gentle and causes only minor damage to the keratin fibers. The direct dyes used for this purpose are subject to many requirements. For example, they must be unobjectionable in toxicological and dermatological terms and must make it possible to attain colorations of a desired intensity which, among other things, presupposes sufficient water solubility. Moreover, the colorations obtained must exhibit good light stability, acid resistance and abrasion resistance.

Compared to oxidative colorations, non-oxidative ones as a rule exhibit lower durability and a less adequate color balance. In addition, direct dyes usually cannot "impart to the hair a brighter shade", because many direct dyes do not tolerate the oxidants needed for brightening and/or the required pH which is higher than or equal to 9.

BRIEF SUMMARY OF THE INVENTION

The goal of the present invention therefore is to provide a colorant—particularly for the blue color range—based on direct dyes that are resistant to basic pH conditions and to oxidants.

We have now found that this goal can be reached by use of certain thiazolium dyes.

DETAILED DESCRIPTION OF THE INVENTION

The present invention therefore has for an object an agent for the simultaneous brightening and dyeing of keratin fibers—particularly hair—characterized in that (a) it contains an oxidant and (b) at least one thiazolium dye of formula (I) and (c) that it has a basic pH

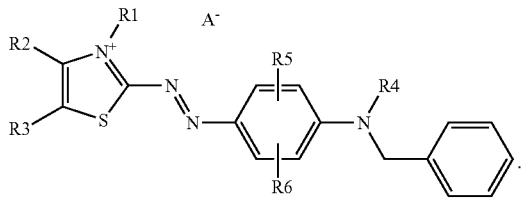

wherein

R1 stands for a saturated or unsaturated $(C_1-C_{12})$-alkyl group, a halogen atom (F, Cl, Br, I)-substituted $(C_1-C_{12})$-alkyl group, a hydroxy-$(C_1-C_{12})$-alkyl group, a $(C_1-C_6)$-alkoxy-$(C_1-C_{12})$-alkyl group, an amino-$(C_1-C_{12})$-alkyl group, a $(C_1-C_6)$-alkylamino-$(C_1-C_{12})$-alkyl group, a di$(C_1-C_6)$-alkylamino-$(C_1-C_{12})$-alkyl group, a cyano-$(C_1-C_{12})$-alkyl group, a substituted or unsubstituted phenyl group or a substituted or unsubstituted benzyl group;

R2 and R3 can be equal or different and independently of each other stand for hydrogen, a halogen atom (F, Cl, Br, I), a saturated or unsaturated $(C_1-C_{12})$-alkyl group, a $(C_1-C_{12})$-alkoxy group, a nitro group, an amino group, a $(C_1-C_{12})$-alkylamino group, a di-$(C_1-C_{12})$-alkylamino group, a $(C_1-C_{12})$-hydroxyalkylamino group, a di$(C_1-C_{12})$-hydroxyalkylamino group, a substituted or unsubstituted phenyl group or a substituted or unsubstituted heteroaryl group;

R4 stands for hydrogen, a saturated or unsaturated $(C_1-C_{12})$-alkyl group, a halogen atom (F, Cl, Br, I)-substituted $(C_1-C_{12})$-alkyl group, a hydroxy-$(C_1-C_{12})$-alkyl group, an amino-$(C_1-C_{12})$-alkyl group or a benzyl group;

R5 and R6 can be equal or different and independently of each other stand for hydrogen, a halogen atom (F, Cl, Br, I), a saturated or unsaturated $(C_1-C_{12})$-alkyl group, a hydroxyl group, a $(C_1-C_{12})$-alkoxy group, a cyano group, a nitro group, an amino group, a $(C_1-C_{12})$-alkylamino group or a di$(C_1-C_{12})$-alkylamino group, and $A^-$ stands for an anion of an organic or inorganic acid.

Preferred among the afore-said compounds of formula (I) are those wherein R1 stands for a saturated or unsaturated $C_1-C_{12}$-alkyl group, the compounds of formula (I) wherein R1 stands for a saturated or unsaturated $(C_1-C_{12})$-alkyl group and R4 stands for a saturated or unsaturated $(C_1-C_{12})$-alkyl group being particularly preferred.

$A^-$ is preferably a chloride, bromide, iodide, hydrogen sulfate, sulfate, toluenesulfonate, benzenesulfonate, monomethylsulfate, hexafluorophosphate, hexafluoroantimonate, tetrafluoroborate, tetraphenylborate, formate, acetate or propionate, the chloride ion, bromide ion, monomethylsulfate ion and acetate ion being particularly preferred.

Suitable compounds of general formula (I) are, for example:
3-methyl-2-[[4-[methyl(phenylmethyl)amino]phenyl]azo]thiazolium chloride, 3-methyl-2-[[4-[methyl(phenylmethyl)amino]phenyl]azo]thiazolium bromide, 3-methyl-2-[[4-[methyl(phenylmethyl)amino]phenyl]azo]thiazolium monomethylsulfate, 3-methyl-2-[[4-[methyl(phenylmethyl)amino]phenyl]azo]thiazolium acetate, 3,4-dimethyl-2-[[4-[methyl(phenylmethyl)amino]phenyl]azo]thiazolium chloride, 3,4-dimethyl-2-[[4-[methyl(phenylmethyl)amino]phenyl]azo]thiazolium bromide, 3,4-dimethyl-2-

[[4-[methyl(phenylmethyl)amino]phenyl]azo]thiazolium monomethylsulfate, 3,4-dimethyl-2-[[4-[methyl(phenylmethyl)amino]phenyl]azo]thiazolium acetate, 3,5-dimethyl-2-[[4-[methyl(phenylmethyl)amino]phenyl]azolium chloride, 3,5-dimethyl-2-[[4-[methyl(phenylmethyl)amino]phenyl]azo]thiazolium bromide, 3,5-dimethyl-2-[[4-[methyl(phenylmethyl)amino]phenyl]azo]thiazolium monomethylsulfate, 3,5-dimethyl-2-[[4-[methyl(phenylmethyl)amino]phenyl]azo]thiazolium acetate, 3,4,5-trimethyl-2-[[4-[methyl(phenylmethyl)amino]phenyl]azo]thiazolium chloride, 3,4,5-trimethyl-2-[[4-[methyl(phenylmethyl)amino]phenyl]azo]thiazolium bromide, 3,4,5-trimethyl-2-[[4-[methyl(phenylmethyl)amino]phenyl]azo]thiazolium monomethylsulfate, 3,4,5-trimethyl-2-[[4-[methyl(phenylmethyl)amino]phenyl]azo]thiazolium acetate, 2-[[4-[ethyl(phenylmethyl)amino]-2-methylphenyl]azo]-3-methylthiazolium chloride, 2-[[4-[ethyl(phenylmethyl)amino]-2-methylphenyl]azo]-3-methylthiazolium bromide, 2-[[4-[ethyl(phenylmethyl)amino]-2-methylphenyl]azo]-3-methylthiazolium monomethylsulfate, 2-[[4-[ethyl(phenylmethyl)amino]-2-methylphenyl]azo]-3-methylthiazolium acetate, 2-[[4-[ethyl(phenylmethyl)amino]-2-methylphenyl]azo]-3,4-dimethylthiazolium chloride, 2-[[4-[ethyl(phenylmethyl)amino]-2-methylphenyl]azo]-3,4-dimethylthiazolium bromide, 2-[[4-[ethyl(phenylmethyl)amino]-2-methylphenyl]azo]-3,4-dimethylthiazolium monomethylsulfate, 2-[[4-[ethyl(phenylmethyl)amino]-2-methylphenyl]azo]-3,4-dimethylthiazolium acetate, 2-[[4-[ethyl(phenylmethyl)amino]-2-methylphenyl]azo]-3,5-dimethylthiazolium chloride, 2-[[4-[ethyl(phenylmethyl)amino]-2-methylphenyl]azo]-3,5-dimethylthiazolium bromide, 2-[[4-[ethyl(phenylmethyl)amino]-2-methylphenyl]azo]-3,5-dimethylthiazolium monomethylsulfate, 2-[[4-[ethyl(phenylmethyl)amino]-2-methylphenyl]azo]-3,5-dimethylthiazolium acetate, 2-[[4-[ethyl(phenylmethyl)amino]-2-methylphenyl]azo]-3,4,5-trimethylthiazolium chloride, 2-[[4-[ethyl(phenylmethyl)amino]-2-methylphenyl]azo-3,4,5-trimethylthiazolium bromide, 2-[[4-[ethyl(phenylmethyl)amino]-2-methylphenyl]azo]-3,4,5-trimethylthiazolium monomethylsulfate, 2-[[4-[ethyl(phenylmethyl)amino]-2-methylphenyl]azo]-3,4,5-trimethylthiazolium acetate, 3-methyl-2-[[4-[(phenylmethyl)amino]phenyl]thiazoazolium chloride, 3-methyl-2-[[4-[(phenylmethyl)amino]phenyl]azo]thiazolium bromide, 3-methyl-2-[[4-[(phenylmethyl)amino]phenyl]azo]thiazolium monomethylsulfate, 3-methyl-2-[[4-[(phenylmethyl)amino]phenyl]azo]thiazolium acetate, 3,4-dimethyl-2-[[4-[(phenylmethyl)amino]phenyl]azo]thiazolium chloride, 3,4-dimethyl-2-[[4-[(phenylmethyl)amino]phenyl]azo]thiazolium bromide, 3,4-dimethyl-2-[[4-[(phenylmethyl)amino]phenyl]azo]thiazolium monomethyl-sulfate, 3,4-dimethyl-2-[[4-[(phenylmethyl)amino]phenyl]azo]thiazolium acetate, 3,5-di-methyl-2-[[4-[(phenylmethyl)amino]phenyl]azo]thiazolium chloride, 3,5-dimethyl-2-[[4-[(phenylmethyl)amino]phenyl]azo]thiazolium bromide, 3,5-dimethyl-2-[[4-[(phenylmethyl)amino]phenyl]azo]thiazolium monomethylsulfate, 3,5-dimethyl-2-[[4-[(phenylmethyl)amino]phenyl]azo]thiazolium acetate, 3,4,5-trimethyl-2-[[4-[(phenylmethyl)amino]phenyl]azo]thiazolium chloride, 3,4,5-trimethyl-2-[[4-[(phenylmethyl)amino]phenyl]azo]thiazolium bromide, 3,4,5-trimethyl-2-[[4-[(phenylmethyl)amino]phenyl]azo]thiazolium monomethylsulfate, 3,4,5-trimethyl-2-[[4-[(phenylmethyl)amino]phenyl]azo]thiazolium acetate, 2-[[4-[bis(phenylmethyl)amino]phenyl]azo]-3-methylthiazolium chloride, 2-[[4-[bis(phenylmethyl)amino]phenyl]azo]-3-methylthiazolium bromide, 2-[[4-[bis(phenylmethyl)amino]-azo]-3-methylthiazolium monomethylsulfate, 2-[[4-[bis(phenylmethyl)amino]phenyl]azo]-3-methylthiazolium acetate, 2-[[4-[bis(phenylmethyl)amino]phenyl]azo]-3,4-dimethylthiazolium chloride, 2-[[4-[bis(phenylmethyl)amino]phenyl]azo]-3,4-dimethylthiazolium bromide, 2-[[4-[bis-(phenylmethyl)amino]phenyl]azo]-3,4-dimethylthiazolium monomethylsulfate, 2-[[4-[bis(phenylmethyl)amino]phenyl]azo]-3,4-dimethylthiazolium acetate, 2-[[4-[bis(phenylmethyl)amino]phenyl]azo]-3,5-dimethylthiazolium chloride, 2-[[4-[bis(phenylmethyl)amino]phenyl]azo]-3,5-dimethylthiazolium bromide, 2-[[4-[bis(phenylmethyl)amino]phenyl]azo]-3,5-dimethylthiazolium monomethylsulfate, 2-[[4-[bis(phenylmethyl)amino]phenyl]azo]-3,5-dimethylthiazolium acetate, 2-[[4-[bis(phenylmethyl)amino]phenyl]azo]-3,4,5-trimethylthiazolium chloride, 2-[[4-[bis(phenylmethyl)amino]phenyl]azo]-3,4,5-trimethylthiazolium bromide, 2-[[4-[bis(phenylmethyl)amino]phenyl]azo]-3,4,5-trimethylthiazolium monomethylsulfate and 2-[[4-[bis(phenylmethyl)amino]phenyl]azo]-3,4,5-trimethylthiazolium acetate.

Particularly preferred compounds of formula (I) are:
3-methyl-2-[[4-[methyl(phenylmethyl)amino]phenyl]azo]thiazolium chloride, 3-methyl-2-[[4-[methyl(phenylmethyl)amino]phenyl]azo]thiazolium bromide, 3-methyl-2-[[4-[methyl(phenylmethyl)amino]phenyl]azo]thiazolium monomethylsulfate, 3-methyl-2-[[4-[methyl(phenylmethyl)amino]phenyl]azo]thiazolium acetate, 3,4-dimethyl-2-[[4-[methyl(phenylmethyl)amino]phenyl]azo]thiazolium chloride, 3,4-dimethyl-2-[[4-[methyl(phenylmethyl)amino]phenyl]azo]thiazolium bromide, 3,4-dimethyl-2-[[4-[methyl(phenylmethyl)amino]phenyl]azo]thiazolium monomethylsulfate, 3,4-dimethyl-2-[[4-[methyl(phenylmethyl)amino]phenyl]azo]thiazolium acetate, 3,5-dimethyl-2-[[4-[methyl(phenylmethyl)amino]phenyl]azo]thiazolium chloride, 3,5-dimethyl-2-[[4-[methyl(phenylmethyl)amino]phenyl]azo]thiazolium bromide, 3,5-dimethyl-2-[[4-[methyl(phenylmethyl)amino]phenyl]azo]thiazolium monomethylsulfate, 3,5-dimethyl-2-[[4-[methyl(phenylmethyl)amino]phenyl]azo]thiazolium acetate, 3,4,5-trimethyl-2-[[4-[methyl(phenylmethyl)amino]phenyl]azo]thiazolium chloride, 3,4,5-trimethyl-2-[[4-[methyl(phenylmethyl)amino]phenyl]azo]thiazolium bromide, 3,4,5-trimethyl-2-[[4-[methyl(phenylmethyl)amino]phenyl]azo]thiazolium monomethylsulfate, 3,4,5-trimethyl-2-[[4-[methyl(phenylmethyl)amino]phenyl]azo]thiazolium acetate, 2-[[4-[ethyl(phenylmethyl)amino]-2-methylphenyl]azo]-3-methylthiazolium chloride, 2-[[4-[ethyl(phenylmethyl)amino]-2-methylphenyl]azo]-3-methylthiazolium bromide, 2-[[4-[ethyl(phenylmethyl)amino]-2-methylphenyl]azo]-3-methylthiazolium monomethylsulfate, 2-[[4-[ethyl(phenylmethyl)amino]-2-methylphenyl]azo]-3-methylthiazolium acetate, 2-[[4-[ethyl(phenylmethyl)amino]-2-methylphenyl]azo]-3,4-dimethylthiazolium chloride, 2-[[4-[ethyl(phenylmethyl)amino]-2-methylphenyl]azo]-3,4-dimethylthiazolium bromide, 2-[[4-[ethyl(phenylmethyl)amino]-2-methylphenyl]azo]-3,4-dimethylthiazolium monomethylsulfate, 2-[[4-[ethyl(phenylmethyl)amino]-2-methylphenyl]azo-3,4-dimethylthiazolium acetate, 2-[[4-[ethyl(phenylmethyl)amino]-2-methylphenyl]azo]-3,5-dimethylthiazolium chloride, 2-[[4-[ethyl(phenylmethyl)amino]-2-methylphenyl]azo-3,5-dimethylthiazolium bromide, 2-[[4-

[ethyl(phenylmethyl)amino]-2-methylphenyl]azo]-3,5-dimethylthiazolium monomethylsulfate, 2-[[4-[ethyl(phenylmethyl)amino]-2-methylphenyl]azo]-3,5-dimethylthiazolium acetate, 2-[[4-[ethyl(phenylmethyl)amino]-2-methylphenyl]azo]-3,4,5-trimethylthiazolium chloride, 2-[[4-[ethyl(phenylmethyl)amino]-2-methylphenyl]azo]-3,4,5-trimethylthiazolium bromide, 2-[[4-[ethyl(phenylmethyl)amino]-2-methylphenyl]azo]-3,4,5-trimethylthiazolium monomethylsulfate and 2-[[4-[ethyl(phenylmethyl)amino]-2-methylphenyl]azo]-3,4,5-trimethylthiazolium acetate.

The colorant of the invention contains the compounds of formula (I) preferably in an amount from 0.01 to 10 weight percent and particularly from 0.1 to 8 weight percent.

Besides the dyes of formula (I), the colorant of the invention can additionally contain other known direct, oxidant-resistant dyes, for example 3-(2',6'-diaminopyridyl-3'-azo)pyridine (=2,6-diamino-3-[(pyridin-3-yl)azo]pyridine), N,N-di(2-hydroxyethyl)-3-methyl-4-[(4-nitrophenyl)azo]aniline (Disperse Red 17; C.I. 11210), 3-diethylamino-7-(4-dimethylaminophenylazo)-5-phenylphenazinium chloride (C.I. 11050), 4-(2-thiazolylazo)resorcinol, 4-[(4-phenylamino)azo]benzenesulfonic acid sodium salt (Orange IV), 1-[(3-aminopropyl)amino]-9,10-anthracenedione (HC Red No. 8), 3',3",4,5,5',5",6,7-octabromophenolsulfonphthalein (Tetrabromophenol Blue), 1-[(4-amino-3,5-dimethylphenyl)-(2,6-dichlorophenyl)methylene]-3,5-dimethyl-4-imino-2,5-cyclohexadiene-phosphoric acid (1:1) (Basic Blue 77), 3',3",5',5"-tetrabromo-m-cresolsulfonphthalein, 2,4-dinitro-1-naphthol-7-sulfonic acid disodium salt (Acid Yellow 1; C.I. 10316), 4-[2'-hydroxy-1'-naphthyl)azo]benzenesulfonic acid sodium salt (Acid Orange 7; C.I. 15510), 3',6'-dihydroxy-2',4',5',7'-tetraiodospiro[isobenzofuran-1(3H),9' (9H)xanthen]-3-one disodium salt (Acid Red 51; C.I. 45430), 6-hydroxy-5-[(2-methoxy-5-methyl-4-sulfophenyl)azo]-2-naphthalenesulfonic acid disodium salt (FD&C Red 40; C.I. 16035), 2,4-dinitro-1-naphthol sodium salt (Acid Yellow 24; C.I. 10315), 2',4',5',7'-tetrabromo-4,5,6,7-tetrachloro-3',6'-dihydroxyspiro{isobenzofuran-1(3H),9'[9H]xanthen}-3-one disodium salt (Acid Red 92; C.I. 45410), 4-(2-hydroxy-1-naphthylazo)-3-methylbenzenesulfonic acid sodium salt (Acid Orange 8; C.I. 15575), 2-amino-1,4-naphthalenedione, dithizone (1,5-diphenylthiocarbazone), N-(2-hydroxyethyl)-2-nitro-4-trifluoromethyl)aniline (HC Yellow 13), N-(2-hydroxyethyl)4-nitroaniline, 4-chloro-N-(2,3-dihydroxypropyl)-2-nitroaniline, 1-methyl-4-[(methylphenylhydrazono)methyl]pyridinium methylsulfate (Basic Yellow No. 87), 3-[(4,5-dihydro-3-methyl-5-keto-1-phenyl-1H-pyrazol-4yl)azo]-N,N,N-trimethylbenzenaminium chloride, 3-[(3-methyl-5-hydroxy-1-phenyl-1H-pyrazol-4-yl)azo]trimethylammoniobenzene chloride (Basic Yellow No. 57), 2-[(4-aminophenyl)azo]-1,3-dimethyl-1H-imidazol-3-ium chloride (Basic Orange No. 31), 1,4-dimethyl-5{[4-(dimethylamino)phenyl]azo}1,2,4-triazolium chloride (Basic Red No. 22); C.I. 11055), 2{[4-(dimethylamino)phenyl]azo}1,3-dimethyl-1H-imidazolium chloride (Basic Red No. 51), 1,4-dimethyl-5-[[4-[methyl(phenylmethyl)amino]phenyl]azo]-1,2,4-triazolium bromide (Basic Red No. 46), N,N,N-trimethyl-3-{[4-(methylamino)-9,10-diketo-9,10-dihydro-1-anthracenyl]amino}-1-propanaminium methylsulfate, N,N-dimethyl-3{[4-(methylamino)-9,10-diketo-9,10-dihydro-1-anthracenyl]amino}-N-propyl-1-propanaminium chloride and N,N-dimethyl-3{[4-(methylamino)-9,10-diketo-9,10-dihydro-1-anthracenyl]-amino}N-propyl-1-propanaminium bromide.

The colorant of the invention contains the dyes of formula (I) and the direct dyes in a total amount of about 0.01 to 15 weight percent and particularly about 0.1 to 12 weight percent.

Naturally, it is also possible to add to the colorant of the invention oxidation precursors, for example o,p,m-phenylenediamines, o,p,m-aminophenols, diphenols or 4,5-diaminopyrazoles.

The colorant can contain these additional developers and couplers in an amount from about 0.01 to 20 wt. %, preferably from about 0.1 to 10 wt. % and particularly from 0.1 to 5 wt. %, each.

The colorant of the invention can be in the form of, for example, a solution, particularly an aqueous or aqueous-alcoholic solution, or a cream, a gel, a surfactant-containing foaming solution (shampoo, aerosol), an emulsion or some other water-containing carrier suitable for use on hair. The colorant of the invention can also be in the form of pellets, granulate or powder which before use are dissolved in an aqueous preparation, for example in water or in an aqueous oxidant preparation.

The composition of these agents consists of a mixture of the dye component with the additives usually employed for such preparations.

Common additives to solutions, creams, emulsions or gels are, for example, solvents such as water, the lower monohydric or polyhydric aliphatic alcohols, the esters and ethers thereof, for example alkanols, particularly those with 1 to 4 carbon atoms, for example ethanol, propanol, isopropanol, butanol and isobutanol, dihydric and trihydric alcohols, particularly those with 2 to 6 carbon atoms, for example ethylene glycol, propylene glycol, 1,3-propanediol, 1,4-butanediol, 1,5-pentanediol, 1,6-hexanediol, 1,2,6-hexanetriol, glycerol, diethylene glycol, dipropylene glycol, polyalkylene glycols such as triethylene glycol, polyethylene glycol, tripropylene glycol, polypropylene glycol, the lower alkyl ethers of polyhydric alcohols such as ethylene glycol monomethyl ether, ethylene glycol monoethyl ether, ethylene glycol monopropyl ether, ethylene glycol monobutyl ether, diethylene glycol monomethyl ether, diethylene glycol monoethyl ether, triethylene glycol monomethyl ether and triethylene glycol monoethyl ether, ketones and keto alcohols, particularly those with 3 to 7 carbon atoms, for example acetone, methyl ethyl ketone, diethyl ketone, methyl isobutyl ketone, methyl phenyl ketone, cyclopentanone, cyclohexanone, diacetone alcohol, ethers, for example dibutyl ether, tetrahydrofuran, dioxane, diisopropyl ether, esters, for example ethyl formate, methyl formate, methyl acetate, ethyl acetate, propyl acetate, butyl acetate, phenyl acetate, ethylene glycol monoethyl ether acetate and hydroxyethyl acetate, amides, for example dimethylformamide and dimethylacetamide, N-methylpyrrolidone as well as urea, tetramethylurea and thiodiglycol.

Moreover, the colorants of the invention can contain wetting agents or emulsifiers from the classes of anionic, cationic, amphoteric, nonionic or zwitterionic surface-active substances, for example fatty alcohol sulfates, ethoxylated fatty alcohol sulfates, alkylsulfonates, alkylbenzenesulfonates, o-olefinsulfonates, alkyltrimethylammonium salts, alkylbetaines, ethoxylated fatty alcohols, ethoxylated nonylphenols, fatty alkanolamides, ethoxylated fatty esters, fatty alcohol polyglycol ether sulfates, alkylpolyglucosides, thickeners such as the higher fatty alcohols, starch, cellulose derivatives, vaselines, paraffin oil, fatty acids and other fat constituents in emulsified form, water-soluble polymeric thickeners such as the natural gums, guar gum, xanthan gum, carob bean flour, pectin, dextran, agar, amylose, amylopectin, dextrins, clays or fully synthetic hydrocolloids, for example polyvinyl alcohol, as well as hair-care agents such as lanolin derivatives, cholesterol, pantothenic acid, water-soluble cationic polymers, protein derivatives, pro-vitamins, vitamins, plant extracts, sugar and betaine, auxiliary agents such as moisturizers, electrolytes, antioxidants, fatty amides, sequestering agents, film-forming agents and preservatives. In addition to water, a water-soluble organic solvent or a mixture of such solvents or a water/solvent mixture can be used.

The said constituents are used in amounts normally employed for such purposes, for example the wetting agents and emulsifiers at a concentration from about 0.1 to 30 wt. %, the thickeners in an amount from about 0.1 to 30 wt. % and the hair-care agents at a concentration from about 0.1 to 5 wt. %.

The ready-to-use colorant of the invention is prepared just before use by mixing the dyes-containing dye carrier composition with an oxidant.

Suitable oxidants are mainly hydrogen peroxide and the compounds of addition thereof to urea, melamine, sodium borate or sodium carbonate in the form of a 1% to 12% and preferably 3% to 9% aqueous solution. The weight ratio of dye carrier composition to oxidant is preferably about 5:1 to 1:3 and particularly 1:1 to 1:2. Larger amounts of oxidant are used primarily with higher concentrations of oxidative dye precursors in the colorant or when it is desired to achieve more pronounced bleaching of the keratin fibers (particularly hair) at the same time. In the event that a brightening of the keratin fibers of up to 6 shade degrees is intended, it is possible to add a persulfate, for example ammonium persulfate, potassium persulfate or sodium persulfate or a mixture thereof, provided that the dyes of formula (I) are resistant to persulfates.

After the dye carrier composition and the oxidant have been mixed, the pH of the ready-to-use colorant assumes a value which depends on the pH of the dye carrier composition and that of the oxidant as well as on the mixing ratio. The ready-to-use agent has a basic pH higher than 7 and preferably a pH of 8 to 11. The adjustment to basic conditions is preferably done with ammonia, although organic amines, for example 2-amino-2-methyl-1-propanol, tris(hydroxymethyl) aminomethane, monoethanolamine and triethanolamine, or mixtures of organic amines and ammonia, as well as inorganic bases such as sodium hydroxide, potassium hydroxide, sodium carbonate, sodium hydrogen carbonate, potassium carbonate, potassium hydrogen carbonate, sodium phosphate, borax ($Na_2B_4O_7 \times 10\ H_2O$) or disodium hydrogen phosphate can be used. Up to the high pH values, the pH can be corrected with an inorganic or organic acid, for example with phosphoric acid, acetic acid, lactic acid, ascorbic acid, citric acid or tartaric acid.

An amount of this mixture sufficient for the coloring treatment is applied to the keratin fibers, generally about 30 to 120 grams, and the mixture is allowed to act on the fibers at about 15 to 50° C., preferably at 30 to 40° C., for about 1 to 60 minutes, preferably 5 to 30 minutes, after which the keratin fibers are rinsed with water and dried. Following this rinsing, the fibers can optionally be washed with a shampoo and possibly post-rinsed with a weak organic acid, for example citric acid or tartaric acid. The keratin fibers are then dried.

It is also possible, when it is necessary to dye hair that has been damaged to different degrees (for example, to re-dye previously oxidatively dyed parts of the hair), to apply to the previously damaged parts of the hair (for example the hair tips) the dye carrier composition without an oxidant in neat form or diluted only with another acidic, neutral or basic aqueous component, and to apply to the undamaged or only slightly damaged parts of hair (for example the hair roots and hair shafts) the mixture of the dye carrier composition and the oxidant. The aqueous component used for dilution can contain the afore-said common additives for solutions, creams, emulsions or gels. By this method, it is possible to achieve colorations adapted to the hair consistency and characterized by a hair-sparing balance between hair roots and hair tips, which is not possible when common oxidative hair colorants are used, because in the latter case an oxidant is always needed for the coupling of the dye precursors.

The colorant of the invention produces colorations that stand out by their special color intensity and brightness, by a good color balance between damaged and undamaged hair (for example between hair tips and newly grown hair) and by very good light stability and perspiration resistance.

Some of the dyes are by themselves known. The dyes of formula (I) can be prepared by methods analogous to the known methods of preparation, for example via azo coupling of 2-aminothiazole derivatives with N-benzylaminophenyl derivatives followed by quaternization, or via oxidative condensation of thiazolone hydrazones with N-benzylaminophenyl derivatives.

The following examples will explain the subject matter of the invention in greater detail without limiting it to the examples.

EXAMPLES

Coloring Examples 1 to 8

Comparative Examples

| | |
|---|---|
| 0.53 g | of dye of formula (I) |
| 5.00 g | of ethanol |
| 4.00 g | of decylglucoside |
| 0.20 g | of ethylenediaminetetraacetic acid disodium salt |
| to 100.00 g | water |

A) According to the Invention 5 g of the foregoing colorant solution was mixed with 5 g of a 9% hydrogen peroxide solution. The colorant solution was adjusted to the desired pH by adding ammonia. The resulting ready-to-use hair colorant was applied to hair having an 80% gray hair content and uniformly distributed with a brush. After a treatment time of 30 min at 40° C., the hair was rinsed with lukewarm water, washed with a shampoo, rinsed with lukewarm water and then dried.

B) Not According to the Invention (Without Hydrogen Peroxide)

5 g of the foregoing colorant solution was mixed with 5 g of water. The colorant solution was adjusted to the desired pH by adding ammonia. The resulting ready-to-use hair colorant was applied to hair having an 80% gray hair content and uniformly distributed with a brush. After a treatment time of 30 min at 40° C., the hair was rinsed with lukewarm water, washed with a shampoo, rinsed with lukewarm water and then dried.

The coloring results are summarized in the following Table 1.

Unless otherwise indicated, all percentages given in the present patent application are by weight.

TABLE 1

| Example | Compound of Formula (I) | pH of Mixture | Shade After Dyeing A: with $H_2O_2$ B: without $H_2O_2$ |
|---|---|---|---|
| 1 | 3-methyl-2-[[4-[methyl(phenylmethyl)amino]-phenyl]azo]thiazolium monomethylsulfate | 9.5 | A: bright cobalt blue B: cobalt blue |
| 2 | 3,4-dimethyl-2-[[4-methyl(phenylmethyl)amino]phenyl]azo]thiazolium monomethylsulfate | 9.3 | A: bright cobalt blue B: cobalt blue |
| 3 | 3,5-dimethyl-2-[[4-methyl(phenylmethyl)amino]phenyl]azo]thiazolium monomethylsulfate | 9.3 | A: bright cobalt blue B: cobalt blue |
| 4 | 3,4,5-trimethyl-2-[[4-methyl(phenylmethyl)-amino]phenyl]azo]thiazolium monomethylsulfate | 9.1 | A: bright cobalt blue B: cobalt blue |
| 5 | 2-[[4-ethyl(phenylmethyl)amino]-2-methylphenyl]azo]-3-methylthiazolium monomethylsulfate | 9.4 | A: bright cobalt blue B: cobalt blue |
| 6 | 2-[[4-ethyl(phenylmethyl)amino]-2-methylphenyl]azo]-3,5-dimethylthiazolium monomethylsulfate | 9.4 | A: bright cobalt blue B: cobalt blue |
| 7 | 2-[[4-ethyl(phenylmethyl)amino]-2-methylphenyl]azo]-3,4-dimethylthiazolium monomethylsulfate | 9.4 | A: bright cobalt blue B: cobalt blue |
| 8 | 2-[[4-ethyl(phenylmethyl)amino]-2-methylphenyl]azo]-3,4,5-trimethylthiazolium monomethylsulfate | 9.4 | A: bright cobalt blue B: cobalt blue |

Examples 9 to 13

Strongly Brightening Colorant

| Brightening Powder Base | |
|---|---|
| 20.0 g | of potassium persulfate |
| 30.0 g | of ammonium persulfate |
| 24.0 g | of sodium silicate |
| 12.5 g | of magnesium oxide |
| 5.0 g | of hydroxycellulose |
| 6.0 g | of soap pellets |
| 2.0 g | of disperse silicic acid |
| 0.5 g | of disodium EDTA |

0.1 g of the dye of formula (I) as per Table 2 was worked into 9.9 g of the brightening powder base. The resulting coloring powder was mixed with 20 g of a 12% aqueous peroxide solution and stirred in a mixing cup until it was homogeneous, after which the mixture was applied to dry, dark-blond natural hair. After a treatment time of 30 min at 40° C., the hair was rinsed with lukewarm water, washed with a shampoo, rinsed with lukewarm water and then dried.

The dyes used and the coloring results are summarized in the following Table 2.

TABLE 2

| Example | Compound of Formula (I) | Shade After Dyeing |
|---|---|---|
| 9 | 3-methyl-2-[[4-[methyl(phenylmethyl)amino]phenyl]-azo]thiazolium monomethylsulfate | steel-blue |
| 10 | 3,5-dimethyl-2-[[4-methyl(phenylmethyl)amino]phenyl]azo]thiazolium monomethylsulfate | steel-blue |
| 11 | 3,4,5-trimethyl-2-[[4-methyl(phenylmethyl)amino]phenyl]azo]thiazolium monomethylsulfate | steel-blue |
| 12 | 2-[[4-ethyl(phenylmethyl)amino]-2-methylphenyl]-azo]-3-methylthiazolium monomethylsulfate | steel-blue |
| 13 | 2-[[4-ethyl(phenylmethyl)amino]-2-methylphenyl]-azo]-3,5-dimethylthiazolium monomethylsulfate | steel-blue |

The invention claimed is:

1. An agent for the simultaneous brightening and coloring of keratin fibers, wherein the agent contains an oxidant and at least one thiazolium dye of formula (I) and has a basic pH

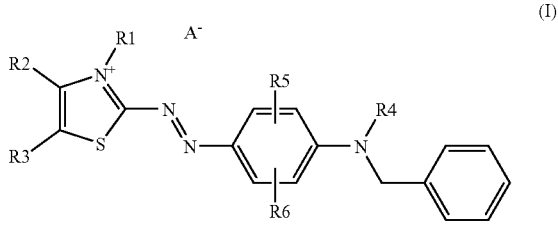

(I)

wherein

R1 stands for a saturated or unsaturated (C1-C12)-alkyl group, a halogen atom-substituted (C1-C12)-alkyl group, a hydroxy-(C1-C12)-alkyl group, a (C1-C6)-alkoxy-(C1-C12)-alkyl group, an amino-(C1-C12)-alkyl group, a (C1-C6)-alkylamino-(C1-C12)-alkyl group, a di(C1-C6)-alkylamino-(C1-C12)-alkyl group, a cyano-(C1-C12)-alkyl group, a substituted or unsubstituted phenyl group or a substituted or unsubstituted benzyl group;

R2 and R3 can be equal or different and independently of each other stand for hydrogen, a halogen atom, a saturated or unsaturated (C1-C12)-alkyl group, a (C1-C12)-alkoxy group, a nitro group, an amino group, a (C1-C12)-alkylamino group, a di(C1-C12)-alkylamino group, a (C1-C12)-hydroxyalkylamino group, a di(C1-C12)-hydroxyalkylamino group, a substituted or unsubstituted phenyl group or a substituted or unsubstituted heteroaryl group;

R4 stands for hydrogen, a saturated or unsaturated (C1-C12)-alkyl group, a halogen atom-substituted (C1-C12)-alkyl group, a hydroxy-(C1-C12)-alkyl group, an amino-(C1-C12)-alkyl group or a benzyl group;

R5 and R6 can be equal or different and independently of each other stand for hydrogen, a halogen atom, a saturated or unsaturated (C1-C12)-alkyl group, a hydroxyl group, a (C1-C12)-alkoxy group, a cyano group, a nitro group, an amino group, a (C1-C12)-alkylamino group or a di(C1-C12)-alkylamino group and A⁻ stands for an anion of an organic or inorganic acid.

2. The agent as defined in claim 1, wherein R1 stands for a saturated or unsaturated (C1-C12)-alkyl group.

3. The agent as defined in claim 2, wherein R4 stands for a saturated or unsaturated (C1-C12)-alkyl group.

4. The agent as defined in claim 1, wherein A⁻ stands for a chloride, bromide, iodide, hydrogen sulfate, sulfate, toluenesulfonate, benzenesulfonate, monomethylsulfate, hexafluorophosphate, hexafluoroantimonate, tetrafluoroborate, tetraphenylborate, formate, acetate or propionate anion.

5. The agent as defined in claim 1, wherein the compound of formula (I) is selected from the group consisting of:
3-methyl-2-[[4-[4-methyl(phenylmethyl)amino]-phenyl]-azo]thiazolium chloride; 3-methyl-2-[[4-[methyl(phenylmethyl)amino]phenyl]azo]thiazolium bromide; 3-methyl-2-[[4-[methyl(phenylmethyl)amino]phenyl]azo]thiazolium monomethyl-sulfate; 3-methyl-2-[[4-[methyl(phenylmethyl)amino]phenyl]azo]thiazolium acetate; 3,4-di-methyl-2-[[4-[methyl(phenylmethyl)amino]phenyl]azo]thiazolium chloride; 3,4-dimethyl-2-[[4-[methyl(phenylmethyl)amino]phenyl]azo]thiazolium bromide; 3,4-dimethyl-2-[[4-[methyl(phenylmethyl)amino]phenyl]azo]thiazolium monomethylsulfate; 3,4-dimethyl-2-[[4-[methyl(phenylmethyl)amino]phenyl]azo]thiazolium acetate; 3,5-dimethyl-2-[[4-[methyl(phenylmethyl)amino]phenyl]azo]thiazolium chloride; 3,5-dimethyl-2-[[4-[methyl(phenylmethyl)amino]phenyl]azo]thiazolium bromide; 3,5-dimethyl-2-[[4-[methyl(phenylmethyl)amino]phenyl]azo]thiazolium monomethylsulfate; 3,5-dimethyl-2-[[4-[methyl(phenylmethyl)amino]phenyl]azo]thiazolium acetate; 3,4,5-trimethyl-2-[[4-[methyl(phenylmethyl)amino]phenyl]azo]thiazolium chloride; 3,4,5-trimethyl-2-[[-4-[methyl(phenylmethyl)amino]phenyl]azo]thiazolium bromide; 3,4,5-trimethyl-2-[[4-[methyl(phenylmethyl)amino]phenyl]azo]thiazolium monomethylsulfate; 3,4,5-trimethyl-2-[[4-[methyl(phenylmethyl)amino]phenyl]thiazolium acetate; 2-[[4-[ethyl(phenylmethyl)amino]-2-methylphenyl]azo]-3-methylthiazolium chloride; 2-[[4-[ethyl(phenylmethyl)amino]-2-methylphenyl]azo]-3-methylthiazolium bromide; 2-[[4-[methyl(phenylmethyl)amino]-2-methylphenyl]azo]-3-methylthiazolium monomethylsulfate; 2-[[4-[ethyl(phenylmethyl)amino]-2-methylphenyl]azo]-3-methylthiazolium acetate; 2-[[4-[ethyl(phenylmethyl)amino]-2-methylphenyl]azo]-3,4-dimethylthiazolium chloride; 2-[[4-[ethyl(phenylmethyl)amino]-2-methylphenyl]azo]-3,4-dimethylthiazolium bromide; 2-[[4-[ethyl(phenylmethyl)amino]-2-methylphenyl]azo]-3,4-dimethylthiazolium monomethylsulfate; 2-[[4-[ethyl(phenylmethyl)amino]-2-methylphenyl]azo]-3,4-dimethylthiazolium acetate; 2-[[4-[ethyl(phenylmethyl)amino]-2-methylphenyl]azo]-3,5-dimethylthiazolium chloride; 2-[[4-[ethyl(phenylmethyl)amino]-2-methylphenyl]azo]-3,5-dimethylthiazolium bromide; 2-[[4-[ethyl(phenylmethyl)amino]-2-methylphenyl]azo]-3,5-dimethylthiazolium monomethylsulfate; 2-[[-4-[ethyl(phenylmethyl)amino]-2-methylphenyl]azo]-3,5-dimethylthiazolium acetate; 2-[[4-[ethyl(phenylmethyl)amino]-2-methylphenyl]azo]-3,4,5-trimethylthiazolium chloride; 2-[[4-[ethyl(phenylmethyl)amino]-2-methylphenyl]azo]-3,4,5-trimethylthiazolium bromide; 2-[[4-[ethyl(phenylmethyl)amino]-2-methylphenyl]azo]-3,4,5-trimethylthiazolium monomethylsulfate; and 2-[[4-[ethyl(phenylmethyl)amino]-2-methylphenyl]azo]-3,4,5-trimethylthiazolium acetate.

6. The agent as defined in claim 1, wherein the agent contains the compound of formula (I) in an amount from 0.01 to 10 weight percent.

7. The agent as defined in claim 1, wherein the agent additionally contains at least one other oxidation-resistant direct dye and/or oxidation dye precursor.

8. The agent as defined in claim 1, wherein the agent is a ready-to-use colorant and has a pH of 8 to 11.

9. The agent as defined in claim 1, wherein the oxidant is selected from among hydrogen peroxide and the compounds of addition thereof to urea, melamine, sodium borate or sodium carbonate.

10. The agent as defined in claim 1, wherein the agent additionally contains a persulfate.

11. The agent as defined in claim 1, wherein the agent is in the form of a 2-component agent consisting of a dye carrier composition (A) containing at least one thiazolium dye of formula (I) and a component (B) containing an oxidant.

12. The agent as defined in claim 1, wherein the agent is a hair colorant.

* * * * *